(12) United States Patent
Neumann

(10) Patent No.: US 11,600,374 B2
(45) Date of Patent: Mar. 7, 2023

(54) SYSTEM AND METHOD FOR GENERATING A CARDIOVASCULAR DISEASE NOURISHMENT PROGRAM

(71) Applicant: KPN INNOVATIONS, LLC., Lakewood, CO (US)

(72) Inventor: Kenneth Neumann, Lakewood, CO (US)

(73) Assignee: KPN INNOVATIONS, LLC., Lakewood, CO (US)

( * ) Notice: Subject to any disclaimer, the term of this patent is extended or adjusted under 35 U.S.C. 154(b) by 0 days.

(21) Appl. No.: 17/136,078

(22) Filed: Dec. 29, 2020

(65) Prior Publication Data

US 2022/0208336 A1    Jun. 30, 2022

(51) Int. Cl.
*G16H 20/60* (2018.01)
*G16H 10/60* (2018.01)
(Continued)

(52) U.S. Cl.
CPC ......... *G16H 20/60* (2018.01); *A61B 5/02007* (2013.01); *A61B 5/4833* (2013.01);
(Continued)

(58) Field of Classification Search
CPC ........ G16H 20/60; G16H 10/60; G16H 50/30; G16H 50/70; G16H 50/20; G06N 20/00; A61B 5/02007; A61B 5/4833
See application file for complete search history.

(56) References Cited

U.S. PATENT DOCUMENTS

| | | |
|---|---|---|
| 7,074,183 B2 | 7/2006 | Castellanos |
| 7,226,792 B2 | 6/2007 | Roberts |

(Continued)

FOREIGN PATENT DOCUMENTS

| | | |
|---|---|---|
| CA | 1318172 A1 | 5/1993 |
| WO | 1999062359 | 12/1999 |
| WO | 2015168252 | 11/2015 |

OTHER PUBLICATIONS https://journals.sagepub.com/doi/full/10.1177/1753944717743920; By: Mark Houston; Jan. 10, 2018; Title: The role of noninvasive cardiovascular testing, applied clinical nutrition and nutritional supplements in the prevention and treatment of coronary heart disease.

(Continued)

*Primary Examiner* — Eliza A Lam
(74) *Attorney, Agent, or Firm* — Caldwell Intellectual Property Law

(57) ABSTRACT

In an aspect, a system for generating a cardiovascular disease nourishment program includes a computing device configured to receive a cardiovascular sample relating to a user, generate a cardiovascular parameter as a function of the cardiovascular disease sample, determine a cardiovascular profile as a function of the a cardiovascular parameter wherein the cardiovascular profile includes a numerical cardiovascular health score correlated to the cardiovascular parameter and an atherosclerosis indicator correlated to the cardiovascular parameter, identify a nutrition element as a function of the cardiovascular profile, wherein identifying comprises obtaining a nutrient composition correlated to a nutrition element, determining a nourishment score as a function of the effect of the nutrition element on the cardiovascular profile, and identifying a nutrition element as a function of the nourishment score and nutrition element machine-learning model, and generate a cardiovascular disease nourishment program as a function of the nourishment score and the cardiovascular profile.

20 Claims, 7 Drawing Sheets

(51) Int. Cl.
  *G16H 50/30* (2018.01)
  *A61B 5/00* (2006.01)
  *G16H 50/20* (2018.01)
  *G06N 20/00* (2019.01)
  *A61B 5/02* (2006.01)
  *G16H 50/70* (2018.01)

(52) U.S. Cl.
  CPC ............ *G06N 20/00* (2019.01); *G16H 10/60* (2018.01); *G16H 50/20* (2018.01); *G16H 50/30* (2018.01); *G16H 50/70* (2018.01)

(56) References Cited

U.S. PATENT DOCUMENTS

| | | | |
|---|---|---|---|
| 9,721,066 B1* | 8/2017 | Funaro | G16H 50/30 |
| 2002/0035316 A1 | 3/2002 | Drazen | |
| 2003/0208108 A1 | 11/2003 | Shewmake | |
| 2005/0032140 A1 | 2/2005 | Kurosawa | |
| 2009/0188796 A1 | 7/2009 | Shewmake | |
| 2009/0246289 A1 | 10/2009 | Superko | |
| 2010/0113892 A1 | 5/2010 | Kaput | |
| 2011/0262939 A1 | 10/2011 | Bergmann | |
| 2012/0003672 A1 | 1/2012 | Bergmann | |
| 2013/0020385 A1 | 1/2013 | Maus | |
| 2016/0198752 A1 | 7/2016 | Mcdonald Cassidy | |
| 2017/0343464 A1 | 11/2017 | Guadagno | |
| 2018/0046770 A1* | 2/2018 | Astigarraga | G16H 20/60 |
| 2018/0342322 A1* | 11/2018 | Apte | G16B 20/00 |
| 2019/0310269 A1* | 10/2019 | Cirulli | G01N 33/6893 |
| 2019/0362848 A1 | 11/2019 | Wolf | |
| 2020/0066181 A1* | 2/2020 | Hadjigeorgiou | G09B 19/0092 |
| 2020/0227172 A1* | 7/2020 | Perkins | G16H 20/30 |
| 2021/0020294 A1* | 1/2021 | Bharmi | G16H 50/30 |
| 2021/0252292 A1* | 8/2021 | Volpe | A61B 5/4836 |

OTHER PUBLICATIONS https://onlinelibrary.wiley.com/doi/epdf/10.1111/j.1365-277X.2008.00889.x; By: J.A. Lovegrove & R. Gitau; Title: Personalized nutrition for the prevention of cardiovascular disease: a future perspective.

https://www.sciencedirect.com/science/article/abs/pii/S0261561416313590; Title: Interaction between a variant of CDKN2A/B-gene with lifestyle factors in determining dyslipidemia and estimated cardiovascular risk: A step toward personalized nutrition; By: Mehrane Mehramiz; Date: Feb. 2018.

https://pubmed.ncbi.nlm.nih.gov/23389112/; Title: A high intake of dietary fiber influences C-reactive protein and fibrinogen, but not glucose and lipid metabolism, in mildly hypercholesterolemic subjects; Date Feb. 2014; By: Anna Johansson-Persson.

https://pubmed.ncbi.nlm.nih.gov/2802434/; Title: Dietary supplementation with low-dose fish oils lowers fibrinogen levels: a randomized, double-blind controlled study; Date: Nov. 1989; By: K Radack.

* cited by examiner

SYSTEM AND METHOD FOR GENERATING A CARDIOVASCULAR DISEASE NOURISHMENT PROGRAM

FIELD OF THE INVENTION

The present invention generally relates to the field of artificial intelligence. In particular, the present invention is directed to methods and systems for generating a cardiovascular disease nourishment program.

BACKGROUND

Current nourishment program generation systems do not account for cardiovascular characteristics of an individual. This leads to inefficiency of a nourishment program generation system and a poor nutrition program for the individual. This is further complicated by a lack of uniformity of nutritional programs, which results in dissatisfaction of individuals.

SUMMARY OF THE DISCLOSURE

In an aspect, a system for generating a cardiovascular disease nourishment program includes a computing device, the computing device configured to receive at least a cardiovascular sample relating to a user. The system is configured to generate at least a cardiovascular parameter as a function of the at least a cardiovascular disease sample, determine a cardiovascular profile as a function of the at least a cardiovascular parameter wherein the cardiovascular profile includes a numerical cardiovascular health score correlated to the at least a cardiovascular parameter wherein the cardiovascular profile includes an atherosclerosis indicator correlated to the at least a cardiovascular parameter, identify at least a nutrition element as a function of the cardiovascular profile, wherein identifying comprises obtaining at least a nutrient composition correlated to at least a nutrition element, determining a nourishment score as a function of the effect of the nutrition element on the cardiovascular profile, and identifying a nutrition element as a function of the nourishment score and nutrition element machine-learning model, and generate a cardiovascular disease nourishment program as a function of the nourishment score and the cardiovascular profile, which includes the cardiovascular health score and the atherosclerosis indicator.

In another aspect, a method for generating a cardiovascular disease nourishment program includes receiving at least a cardiovascular sample relating to a user, generating at least a cardiovascular parameter as a function of the at least a cardiovascular disease sample, determining a cardiovascular profile as a function of the at least a cardiovascular parameter wherein the cardiovascular profile includes a numerical cardiovascular health score correlated to the at least a cardiovascular parameter wherein the cardiovascular profile includes an atherosclerosis indicator correlated to the at least a cardiovascular parameter, identifying at least a nutrition element as a function of the cardiovascular profile, wherein identifying comprises obtaining at least a nutrient composition correlated to at least a nutrition element, determining a nourishment score as a function of the effect of the nutrition element on the cardiovascular profile, and identifying a nutrition element as a function of the nutrient composition, nourishment score, and nutrition element machine-learning model, and generating a cardiovascular disease nourishment program as a function of the nourishment score and the cardiovascular profile, which includes the cardiovascular health score and the atherosclerosis indicator.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein.

The drawings are not necessarily to scale and may be illustrated by phantom lines, diagrammatic representations and fragmentary views. In certain instances, details that are not necessary for an understanding of the embodiments or that render other details difficult to perceive may have been omitted.

DETAILED DESCRIPTION

At a high level, aspects of the present disclosure are directed to systems and methods for generating a cardiovascular disease nourishment program. In an embodiment, the disclosure may receive at least a cardiovascular disease sample relating to a user. Aspects of the present disclosure can be used to generate at least a cardiovascular parameter as a function of the cardiovascular disease sample. Aspects of the present disclosure can also be used to determine a cardiovascular profile including a numerical cardiovascular health score and atherosclerosis indicator. Aspects of the present disclosure can be used to identify at least a nutrition element as a function of the cardiovascular profile. This may be so, at least in part, because the embodiments may utilize a nutrition element machine-learning model. Aspects of the present disclosure allow for generating a cardiovascular nourishment program. Exemplary embodiments illustrating aspects of the present disclosure are described below in the context of several specific examples.

Figure 1:
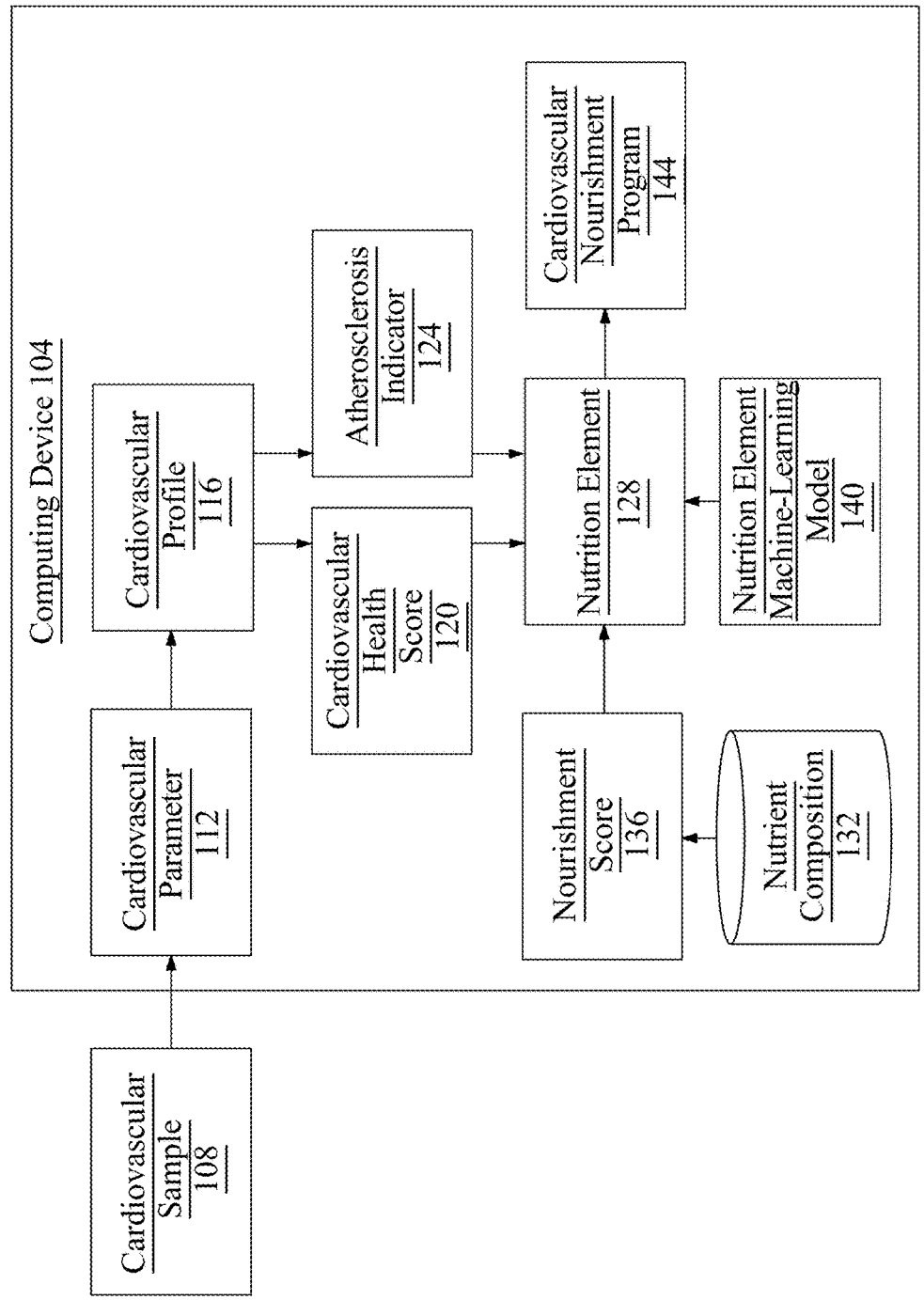
FIG. 1 is a block diagram illustrating an exemplary embodiment of a system for generating a cardiovascular disease nourishment program.

Referring now to FIG. 1, an exemplary embodiment of a system 100 for generating a cardiovascular disease nourishment program is illustrated. System includes a computing device 104. Computing device 104 may include any computing device as described in this disclosure, including without limitation a microcontroller, microprocessor, digital signal processor (DSP) and/or system on a chip (SoC) as described in this disclosure. Computing device 104 may include, be included in, and/or communicate with a mobile device such as a mobile telephone or smartphone. Computing device 104 may include a single computing device operating independently, or may include two or more computing device operating in concert, in parallel, sequentially or the like; two or more computing devices may be included together in a single computing device or in two or more computing devices. Computing device 104 may interface or communicate with one or more additional devices as described below in further detail via a network interface device. Network interface device may be utilized for connecting computing device 104 to one or more of a variety of networks, and one or more devices. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network may employ a wired and/or a wireless mode of communication. In general, any network topology may be used. Information (e.g., data, software etc.) may be communicated to and/or from a computer and/or a computing device. computing device 104 may include but is not limited to, for example, a computing device or cluster of computing devices in a first location and a second computing device or cluster of computing devices in a second location. computing device 104 may include one or more computing devices dedicated to data storage, security, distribution of traffic for load balancing, and the like. computing device 104 may distribute one or more computing tasks as described below across a plurality of computing devices of computing device, which may operate in parallel, in series, redundantly, or in any other manner used for distribution of tasks or memory between computing devices. computing device 104 may be implemented using a "shared nothing" architecture in which data is cached at the worker, in an embodiment, this may enable scalability of system 100 and/or computing device.

With continued reference to FIG. 1, computing device 104 may be designed and/or configured to perform any method, method step, or sequence of method steps in any embodiment described in this disclosure, in any order and with any degree of repetition. For instance, computing device 104 may be configured to perform a single step or sequence repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. computing device 104 may perform any step or sequence of steps as described in this disclosure in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

With continued reference to FIG. 1, a system for generating a cardiovascular disease nourishment program, the system comprising a computing device 104, the computing device 104 configured to receive at least a cardiovascular sample 108 relating to a user. A "cardiovascular sample", for the purposes of this disclosure, is an element submitted to the system by a user relating to a cardiovascular disease state relating to the user. The cardiovascular sample 108 includes receiving a result of one or more tests relating the user. The tests relating to a user may include blood pressure test, blood lipid panel, Type I diabetes test, Type II diabetes test, electrocardiogram (EKG), echocardiogram (ECG), chest X-rays, cardiac catheterization, angiogram, magnetic resonance imaging (MM), magnetic resonance angiography (MRA), angiography, computerized tomography (CT), transesophageal echocardiogram (TEE), Holter Monitor, Cardiac Enzymes tests, including troponin tests, full blood count (FBC), stress test (treadmill or stationary bike, among others), ultrasound, and coronary calcium scans. Receiving at least a cardiovascular sample 108 includes receiving a prior diagnosis of cardiovascular disease relating to a user. A "prior diagnosis", for the purposes of this disclosure, is a cardiovascular disease state relating to a user that was previously identified, for instance by a previous iteration of processes described in this disclosure, by a doctor or other medical professional, or the like; wherein the user may for instance have been diagnosed with a cardiovascular disease or condition. Prior diagnosis of a cardiovascular disease may include prior diagnosis of arrythmias, aorta disease, Marfan Syndrome, congenital heart disease, coronary artery disease, deep vein thrombosis, pulmonary embolism, heart attack, heart failure, cardiomyopathy, heart valve disease, pericardial disease, peripheral vascular disease, rheumatic heart disease, stroke, vascular (blood vessel) disease, hypertension (high blood pressure), and hypercholesterolemia (high cholesterol). Cardiovascular sample 108 may include receiving a cardiovascular signal from a sensor. A "cardiovascular signal" is a datum that relates to and/or represents an element associated with the status of an individual's cardiovascular system. As a non-limiting example, a cardiovascular signal may include an image of a heart, veins, or arteries. As a further non-limiting example, a cardiovascular signal may include one or more lights, voltages, currents, sounds, chemicals, pressures, and the like from a sensor. "Sensors" for the purposes of this disclosure, refers to a device that records, monitors, stores, measures, and/or transmits cardiovascular signals. As a non-limiting example, a sensor may include an imaging sensors, such as optical cameras, infrared cameras, 3D cameras, multispectral cameras, hyperspectral cameras, polarized cameras, chemical sensors, motion sensors, ranging sensors, light radar components, detection or imaging using radio frequency component like radar, terahertz or millimeter waves imagers, seismic sensors, magnetic sensors, weight/mass sensors, ionizing radiation sensors, and/or acoustical sensors. AS a further non-limiting example, a sensor may include one or more medical devices that at least detect and/or monitor an individual's cardiovascular system, such as semi-auto analyzers, photo colorimeters, cell photo colorimeters, hemoglobin meters, mass spectrometers, chromatographic instruments, and the like. Cardiovascular sample 108 may include other biomarkers relating to a user that would indicate a cardiovascular disease such as HsCRP, LPLAC2, MPO, Lp(a), lipid particle fractionation, microbiome, cardiac flow imaging, troponin levels, exercise stress test, echocardiogram, cTn, hs-cTn, H-FABP, GDF-15, fibrinogen, UA, Papp-A, MMPs, Lp-PLA2, sPLA2, sCD40L, copeptin, MR-proADM, NPs, ST2, ET-1, Gal-3, NRG-1, MicroRNAs, and the like. Cardiovascular sample 108 may include biomarkers relating to symptoms of a cardiovascular disease such as extreme fatigue, dizziness, lightheadedness, fast heart rate, chest pain during activity, difficulty breathing, confusion, loss of appetite, nausea, and changes of sleep pattern.

Computing device 104 generates at least a cardiovascular parameter 112 of a plurality of cardiovascular parameters 112 as a function of the cardiovascular disease sample 108. A "cardiovascular parameter", for the purposes of this disclosure, is a measurable value associated with a user's cardiovascular system. As a non-limiting example, cardiovascular parameters may include blood pressure, resting heart rate, cholesterol level, body fat percentage, one or more chemical concentrations, cardiac index, Left Atrial Pressure (LAP), Cardiac Output (CO), Stroke Volume (SV), among other hemodynamic parameters. Cardiovascular parameter 112 may be generated as a function of a cardiovascular algorithm. A cardiovascular algorithm may include Framingham-hard-Cardiovascular Endpoints (FRS-hard-CVE), Framingham CHD1 (FRS-CHD1), Framingham CHD2 (FRS-CHD2), Framingham CVD (FRS-CVD), ARRIBA, PROCAM I, PROCAM II, Reynolds score, ESC Heart Score (ESC-HS) and atherosclerotic cardiovascular disease score (ASCVD), sometimes called Pooled Cohort Equation, cardiac output Fick's method, cerebral perfusion pressure, mean arterial pressure, stroke volume, maximum heart rate, heart rate on an EKG strip, respiratory quotient, systemic vascular resistance, pulmonary vascular resistance, static compliance, dynamic compliance, dead space to tidal volume ratio, children dosage estimation, infant dosage estimation, infant and children dosage estimation, anion gap, body surface area elastance, smoking use calculation, suction catheter size estimation, endotracheal tube size estimation in children, Boyle's law, Charles' law, Gay-Lussac's law, LaPlace's law, Celsius to Fahrenheit temperature conversion, Fahrenheit to Celsius temperature conversion, Celsius to Kelvin temperature conversion, helium/oxygen conversion, total lung capacity, pressure support ventilator setting, rapid shallow breathing index, endotracheal tube size estimation in children, minimum flow rate in mechanical ventilation, and the like thereof.

Still referring to FIG. 1, computing device 104 determines cardiovascular profile 116 as a function of the at least a cardiovascular parameter 112 wherein the cardiovascular profile 116. "Cardiovascular profile", for the purposes of this disclosure, refers to a profile of a user's cardiovascular state of health according to a plurality of cardiovascular parameters. Cardiovascular profile 116, as a non-limiting example, may include cholesterol level, resting heart rate, and blood pressure. Cardiovascular profile 116 may include parameters chosen specifically due to a cardiovascular deficiency. "Cardiovascular deficiency", for the purposes of this disclosure, is an inadequacy and/or deficiency of a cardiovascular parameter compared to a cardiovascular threshold. "Cardiovascular threshold", for the purposes of this disclosure, refers to a range of a cardiovascular parameter, limit, maximum, or minimum thereof that constitutes healthy or normal cardiovascular parameter 112. Cardiovascular threshold may be defined, in a non-limiting example, by American Medical Association, American College of Physicians, American Heart Association, and American College of Cardiology, among others. Cardiovascular threshold may be defined, in a further non-limiting example, in guidelines included in one or more medical journals, such as the Lancet, New England Journal of Medicine, Science, Journal of American Medical Association, and the like thereof.

Still referring to FIG. 1, cardiovascular profile 116 includes a numerical cardiovascular health score 120. "Cardiovascular health score" for the purposes of this disclosure, refers to may be a quantitative value assigned to cardiovascular profile as a function of the cardiovascular parameters and their relationship to the cardiovascular threshold associated with the cardiovascular parameter. In a non-limiting example, cholesterol may be a cardiovascular parameter, and be assigned a first weight. Cholesterol level may be above the maximum defined in cholesterol cardiovascular threshold and would then be given a numerical score. This would be done to a plurality of cardiovascular parameters 112 within cardiovascular profile 116 and then summed to produce cardiovascular health score 120. The weights associated with each cardiovascular parameter may be personalized to the user, or the same for every user.

Still referring to FIG. 1, cardiovascular profile 116 includes atherosclerosis indicator 124 correlated to at least a cardiovascular parameter 112. An "atherosclerosis indicator", for the purposes of this disclosure, is a qualitative or quantitative element of data that indicates the presence and location of fatty deposits in a vein or artery wall. "Fatty deposits", for the purposes of this disclosure, refers to the deposition of plaque, cholesterol, fatty substances, cellular waste products, calcium, and fibrin. Atherosclerosis indicator 124 may include a location in the user's body wherein a vein or artery is accumulating plaque buildup. Atherosclerosis indicator 124 may be consistent with any of the above parameters, biomarkers, or the like. Atherosclerosis indicator 124 may be a test result or prior diagnosis indicating atherosclerosis. Atherosclerosis indicator 124 may be a specific indication of atherosclerosis, such as blood pressure, coronary embolism, stroke, heart attack, or other cardiovascular parameters 116.

Still referring to FIG. 1, computing device 104 identifies at least a nutrition element 128 as function of the cardiovascular profile 116. "Nutrition element", as used in this disclosure, refers to a source of nourishment that may be consumed by a user such that the user may absorb nutrients from the nutrition element. In a non-limiting example, nutrition element 128 may include plants, meats, animal products, fungi, seeds, nuts, legumes, fruits, dairy, milk, eggs, cereals, grains, seafood, dried foods, dumplings, pies, noodles, salads, stews, soups, sauces, sandwiches, and the like. Computing device 104 may identify the plurality of nutrition elements 128 by classifying the cardiovascular profile 116 to a cardiovascular disease category. A "cardiovascular disease category", for the purposes of this disclosure, is a grouping of diseases by some common element of cardiovascular disease. In a non-limiting example, a category of cardiovascular disease may be genetic diseases, onset diseases, or environmental diseases. Computing device 104 may then identify the plurality of nutrition elements 128 according to the cardiovascular disease category, wherein the plurality of nutrition elements may be specifically tailored to that category. Computing device 104 obtains at least a nutrient composition 132 correlated to at least a nutrition element 128. Nutrient composition 132 may include a list and/or compilation of all of the nutrients contained in a nutrition element 128. Nutrient composition 132 may include one or more quantities and/or amounts of total fat, including saturated fat and/or trans-fat, cholesterol, sodium, total carbohydrates, including dietary fiber and/or total sugars, protein, vitamin A, vitamin C, thiamin, riboflavin, niacin, pantothenic acid, vitamin b6, folate, biotin, vitamin B12, vitamin D, vitamin E, vitamin K, calcium, iron, phosphorous, iodine, magnesium, zinc, selenium, copper, manganese, chromium, molybdenum, chloride, and the like thereof. Nourishment composition 132 may be obtained from a directory, database, library, or other data store where nutrient composition 132 may be stored. Computing device 104 may determine a nourishment score 136 as a function of the effect of the nutrition element 128 on the cardiovascular profile 116. A "nourishment score", for the purposes of this disclosure, is a quantitative value associated with the effectiveness of the nutrition element, which is comprised of nutrients, on the cardiovascular profile.

With continued reference to FIG. 1, determining nourishment scores 136 by generating training data using the plurality of nutrition elements 128 identified according to the cardiovascular disease category. Training data may be generated in a plurality of methods including, but not limited to: databases, datastores, expert inputs, hospital records, medical records, test results, prior diagnoses data, and user inputs, among others. Training data may correlate machine-learning model inputs to machine-learning model outputs consistent with the entirety of this disclosure. Computing device 104 trains a nutrition element machine-learning model 140 according to the training data entries that correlate the nourishment score 136 for each cardiovascular disease category to nutrient composition 132.

Still referring to FIG. 1, nutrition element machine-learning model may include a machine-learning model configured to produce a nutrition element output given nourishment compositions and nourishment deficiencies as inputs; this is in contrast to a non-machine learning software program where the commands to be executed are determined in advance by a user and written in a programming language. Nutrition element machine-learning model 140 may include one or more nutrition element machine-learning processes such as supervised, unsupervised, or reinforcement machine-learning processes that computing device 104 and/or a remote device may or may not use in the determination of nutrition element 128. As used in this disclosure "remote device" is an external device to computing device 104. An nutrient element machine-learning process may include, without limitation machine learning processes such as simple linear regression, multiple linear regression, polynomial regression, support vector regression, ridge regression, lasso regression, elasticnet regression, decision tree regression, random forest regression, logistic regression, logistic classification, K-nearest neighbors, support vector machines, kernel support vector machines, naïve bayes, decision tree classification, random forest classification, K-means clustering, hierarchical clustering, dimensionality reduction, principal component analysis, linear discriminant analysis, kernel principal component analysis, Q-learning, State Action Reward State Action (SARSA), Deep-Q network, Markov decision processes, Deep Deterministic Policy Gradient (DDPG), or the like thereof.

Still referring to FIG. 1, computing device 104 may train nutrition element machine-learning process as a function of a nutrition element training set. As used in this disclosure a "nutrition element training set" is a training set that correlates at least nourishment composition and nourishment deficiency to a nutrition element 128. For example, and without limitation, nourishment composition of 14 g of protein and 2 g of fiber and a nourishment deficiency of low levels of protein CC16 as a function of chronic heart disease may relate to an nutrition element of salmon. The nutrition element training set may be received as a function of user-entered valuations of nourishment compositions, nourishment deficiencies, and/or nutrition elements. Computing device 104 may receive nutrition element training set by receiving correlations of nourishment compositions and/or nourishment deficiencies that were previously received and/or determined during a previous iteration of determining nutrition elements. The nutrition element training set may be received by one or more remote devices that at least correlate a nourishment composition and nourishment deficiency to a nutrition element 128, wherein a remote device is an external device to computing device 104, as described above.

Still referring to FIG. 1, nutrition element machine-learning model 140 may identify nutrition element 128 as a function of one or more classifiers. A "classifier," as used in this disclosure is a machine-learning model, such as a mathematical model, neural net, or program generated by a machine learning algorithm known as a "classification algorithm," as described in further detail below, that sorts inputs into categories or bins of data, outputting the categories or bins of data and/or labels associated therewith. A classifier may be configured to output at least a datum that labels or otherwise identifies a set of data that are clustered together, found to be close under a distance metric as described below, or the like. Computing device 104 and/or another device may generate a classifier using a classification algorithm, defined as a processes whereby a computing device 104 derives a classifier from training data. Classification may be performed using, without limitation, linear classifiers such as without limitation logistic regression and/or naive Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers.

Still referring to FIG. 1, computing device 104 may be configured to generate a classifier using a Naïve Bayes classification algorithm. Naïve Bayes classification algorithm generates classifiers by assigning class labels to problem instances, represented as vectors of element values. Class labels are drawn from a finite set. Naïve Bayes classification algorithm may include generating a family of algorithms that assume that the value of a particular element is independent of the value of any other element, given a class variable. Naïve Bayes classification algorithm may be based on Bayes Theorem expressed as $P(A/B)=P(B/A) P(A)+P(B)$, where P(AB) is the probability of hypothesis A given data B also known as posterior probability; P(B/A) is the probability of data B given that the hypothesis A was true; P(A) is the probability of hypothesis A being true regardless of data also known as prior probability of A; and P(B) is the probability of the data regardless of the hypothesis. A naïve Bayes algorithm may be generated by first transforming training data into a frequency table. Computing device 104 may then calculate a likelihood table by calculating probabilities of different data entries and classification labels. Computing device 104 may utilize a naïve Bayes equation to calculate a posterior probability for each class. A class containing the highest posterior probability is the outcome of prediction. Naïve Bayes classification algorithm may include a gaussian model that follows a normal distribution. Naïve Bayes classification algorithm may include a multinomial model that is used for discrete counts. Naïve Bayes classification algorithm may include a Bernoulli model that may be utilized when vectors are binary.

With continued reference to FIG. 1, computing device 104 may be configured to generate a classifier using a K-nearest neighbors (KNN) algorithm. A "K-nearest neighbors algorithm" as used in this disclosure, includes a classification method that utilizes feature similarity to analyze how closely out-of-sample-features resemble training data to classify input data to one or more clusters and/or categories of features as represented in training data; this may be performed by representing both training data and input data in vector forms, and using one or more measures of vector similarity to identify classifications within training data, and to determine a classification of input data. K-nearest neighbors algorithm may include specifying a K-value, or a number directing the classifier to select the k most similar entries training data to a given sample, determining the most common classifier of the entries in the database, and classifying the known sample; this may be performed recursively and/or iteratively to generate a classifier that may be used to classify input data as further samples. For instance, an initial set of samples may be performed to cover an initial heuristic and/or "first guess" at an output and/or relationship, which may be seeded, without limitation, using expert input received according to any process as described herein. As a non-limiting example, an initial heuristic may include a ranking of associations between inputs and elements of training data. Heuristic may include selecting some number of highest-ranking associations and/or training data elements.

With continued reference to FIG. 1, generating k-nearest neighbors algorithm may generate a first vector output containing a data entry cluster, generating a second vector output containing an input data, and calculate the distance between the first vector output and the second vector output using any suitable norm such as cosine similarity, Euclidean distance measurement, or the like. Each vector output may be represented, without limitation, as an n-tuple of values, where n is at least two values. Each value of n-tuple of values may represent a measurement or other quantitative value associated with a given category of data, or attribute, examples of which are provided in further detail below; a vector may be represented, without limitation, in n-dimensional space using an axis per category of value represented in n-tuple of values, such that a vector has a geometric direction characterizing the relative quantities of attributes in the n-tuple as compared to each other. Two vectors may be considered equivalent where their directions, and/or the relative quantities of values within each vector as compared to each other, are the same; thus, as a non-limiting example, a vector represented as [5, 10, 15] may be treated as equivalent, for purposes of this disclosure, as a vector represented as [1, 2, 3]. Vectors may be more similar where their directions are more similar, and more different where their directions are more divergent; however, vector similarity may alternatively or additionally be determined using averages of similarities between like attributes, or any other measure of similarity suitable for any n-tuple of values, or aggregation of numerical similarity measures for the purposes of loss functions as described in further detail below. Any vectors as described herein may be scaled, such that each vector represents each attribute along an equivalent scale of values. Each vector may be "normalized," or divided by a "length" attribute, such as a length attribute l as derived using a Pythagorean norm: $l=\sqrt{\Sigma_{i=0}^{n} a_i^2}$, where $a_i$ is attribute number i of the vector. Scaling and/or normalization may function to make vector comparison independent of absolute quantities of attributes, while preserving any dependency on similarity of attributes; this may, for instance, be advantageous where cases represented in training data are represented by different quantities of samples, which may result in proportionally equivalent vectors with divergent values.

Still referring to FIG. 1, computing device 104 may receive nutrition element machine-learning model 140 from the remote device that utilizes one or more nutrition element machine learning processes, wherein a remote device is described above in detail. For example, and without limitation, a remote device may include a computing device, external device, processor, and the like thereof. The remote device may perform the nutrition element machine-learning process using the nutrition element training set to generate nutrition element 128 and transmit the output to computing device 104. The remote device may transmit a signal, bit, datum, or parameter to computing device 104 that at least relates to nutrition element 128. Additionally or alternatively, the remote device may provide an updated machine-learning model. For example, and without limitation, an updated machine-learning model may be comprised of a firmware update, a software update, an nutrition element machine-learning process correction, and the like thereof. As a non-limiting example a software update may incorporate a new nourishment composition that relates to a modified nourishment deficiency. Additionally or alternatively, the updated machine learning model may be transmitted to the remote device, wherein the remote device may replace the nutrition element machine-learning model with the updated machine-learning model and determine the nutrition element 128 as a function of the nourishment deficiency using the updated machine-learning model. The updated machine-learning model may be transmitted by the remote device and received by computing device 104 as a software update, firmware update, or corrected nutrition element machine-learning model. For example, and without limitation a nutrition element machine-learning model may utilize a neural net machine-learning process, wherein the updated machine-learning model may incorporate polynomial regression machine-learning process. Updated machine learning model may additionally or alternatively include any machine-learning model used as an updated machine learning model as described in U.S. Nonprovisional application Ser. No. 17/106,658, filed on Nov. 30, 2020, and entitled "A SYSTEM AND METHOD FOR GENERATING A DYNAMIC WEIGHTED COMBINATION," the entirety of which is incorporated herein by reference.

Computing device 104 determines nourishment score as a function of the nutrition element machine-learning model 140 and the cardiovascular profile 116. Nourishment score 136 may indicate that a nutrition element 128 has a positive effect on cardiovascular profile 116. Nourishment score 136 may be higher for nutrition elements 128 that raise cardiovascular health score 120. Identifying nutrition element 128 as a function of the nourishment score 136 and nutrition element machine-learning model 140. Identifying the plurality of nutrition elements 128 may include curating nutrition elements 128 intended to prevent cardiovascular disease according to the cardiovascular disease category. Curating nutrition elements may include suggesting nutrition elements that improve cardiovascular disease by improving the common element in cardiovascular disease category. For example, nutrition elements that lower cholesterol may be suggested for a cardiovascular disease category wherein high cholesterol is the common element. In a non-limiting embodiment, leafy green vegetables may be suggested as nutrition elements to lower cholesterol in a user that has heart disease, wherein high cholesterol is a cardiovascular parameter.

Still referring to FIG. 1, computing device 104 generates nourishment program 144 as a function of the nourishment score 136 and the cardiovascular profile 116. A "cardiovascular disease nourishment program", for the purposes of this disclosure, is a suggested nourishment program that may include foods, meals, supplements, vitamins, and minerals, among others, intended to improve the cardiovascular disease state of the user. Generating the cardiovascular disease nourishment program 144 may include generating an adherence score, wherein the adherence score reflects the level of user participation in the cardiovascular nourishment program. Adherence may be measured by user input to a meal tracker application, notebook, list, computer application, or the like. Adherence score may grant points to a user for following a suggested meal plan, such as cardiovascular disease nourishment plan 144. Adherence score, in a non-limiting example, may include weighted values which value some nutrition elements 128 more than others, and that weight may be correlated to nourishment score 136. Adherence score may seek to maximize nourishment score 136 in any subset of nourishment program 144. Adherence score may include calculating a change in numerical cardiovascular health score 120, wherein a positive change in health score 120 over a period of time would indicate a high adherence score and a negative change in health score 120 would indicate a low adherence score. In non-limiting embodiments, adherence score may be generated at the generation of nourishment program 144 and consistently and periodically updated throughout the nourishment program 144.

Still referring to FIG. 1, computing device 104 may generate cardiovascular disease nourishment program 144, wherein generating cardiovascular disease nourishment program 144 may include receiving at least a user preference regarding the at least a nutrition element 128. The user preference may include user selection of nutrition elements 128 like foods the user prefers, food the user wishes to not consume, food alternates, wherein a user may select a food nutritionally similar to a suggested nutrition element, allergy requirements, food intolerance preferences, and the like. User preferences may increase adherence score by including foods a user is more likely to eat and excluding foods a user cannot or will not consume. Computing device 104 may modify nutrition element 128 as a function of the user preference. Computing device 104 may modify cardiovascular nourishment program 144 by switching, adding, deleting, or otherwise altering nutrition elements 128 within the program.

Still referring to FIG. 1, computing device 104 may generate cardiovascular disease nourishment program 144 by generating a nourishment program classifier using a classification machine-learning process to classify nutrition elements 128 by the plurality of nutrient compositions 132. Computing device 104 may then compile the plurality of nutrition elements 128 to achieve the nourishment score 136, wherein the nourishment score 136 may be sought to be maximized to benefit the user. High nourishment score 136 may increase adherence score and therefore also cardiovascular health score 120.

Still referring to FIG. 1, computing device 104 may train classification machine-learning process as a function of a nourishment training set. As used in this disclosure a "nourishment training set" is a training set that correlates a nutrition elements to nutrient compositions. The nourishment training set may be received as a function of user-entered nutrition elements 128, intendent outcomes, and/or nourishment programs. Computing device 104 may receive nourishment training by receiving correlations of nutrition elements and nutrient compositions that were previously received and/or determined during a previous iteration of determining nourishment programs. Nourishment training set may be generated by any of the methods disclosed hereinabove, or another method undisclosed. The nourishment training set may be received by one or more remote devices that correlate a nutrition element and/or nutrient compositions to a nourishment program, wherein a remote device is an external device to computing device 104, as described above.

Still referring to FIG. 1, computing device 104 may receive classification machine-learning model from the remote device that utilizes one or more classification machine learning processes, wherein a remote device is described above in detail. For example, and without limitation, a remote device may include a computing device, external device, processor, and the like thereof. The remote device may perform the classification machine-learning process using the nourishment training set to generate nourishment program 144 and transmit the output to computing device 104. The remote device may transmit a signal, bit, datum, or parameter to computing device 104 that at least relates to nourishment program 144. Additionally or alternatively, the remote device may provide an updated machine-learning model. For example, and without limitation, an updated machine-learning model may be comprised of a firmware update, a software update, a classification machine-learning process correction, and the like thereof. As a non-limiting example a software update may incorporate a new intended outcome that relates to a modified edible. Additionally or alternatively, the updated machine learning model may be transmitted to the remote device, wherein the remote device may replace the classification machine-learning model with the updated machine-learning model and determine the nourishment program as a function of the intended outcome using the updated machine-learning model. The updated machine-learning model may be transmitted by the remote device and received by computing device 104 as a software update, firmware update, or corrected classification machine-learning model. For example, and without limitation classification machine-learning model may utilize a nearest neighbor machine-learning process, wherein the updated machine-learning model may incorporate association rules machine-learning processes.

Figure 2:
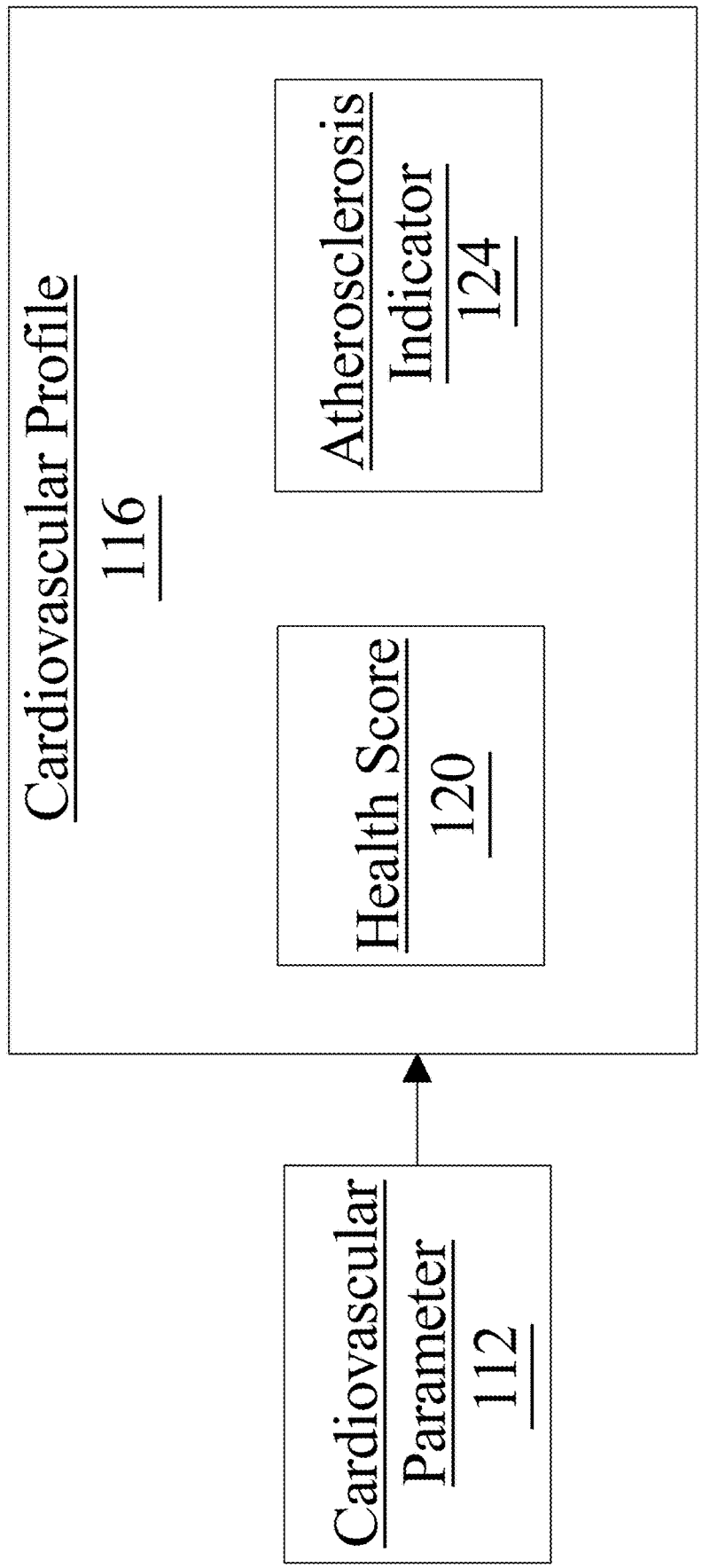
FIG. 2 is a representative diagram of an exemplary embodiment of cardiovascular parameters according to an embodiment of the invention.

Now referring to FIG. 2, cardiovascular profile 116 may include cardiovascular health score 120. Cardiovascular profile 116 may include atherosclerosis indicator 124. Cardiovascular health score 120 may be a numerical value that acts as a summary of a user's cardiovascular health as a function of the plurality of cardiovascular parameters 112 and their respective cardiovascular thresholds. Any number or combination of mathematical manipulations may be performed on any number or combination of cardiovascular parameters 112 to generate cardiovascular health score 120. Atherosclerosis indicator 124 may include a location, severity, type, and age of atherosclerosis. Atherosclerosis indicator 124 may include how long plaque or fatty deposits have been present in arteries and may suggest what treatment would be suitable for the user based on atherosclerosis indicator 124. Cardiovascular profile 116, which is determined as a function of cardiovascular parameters 112, may be updated over time to reflect improvement or decline in user's cardiovascular disease state condition.

Figure 3:
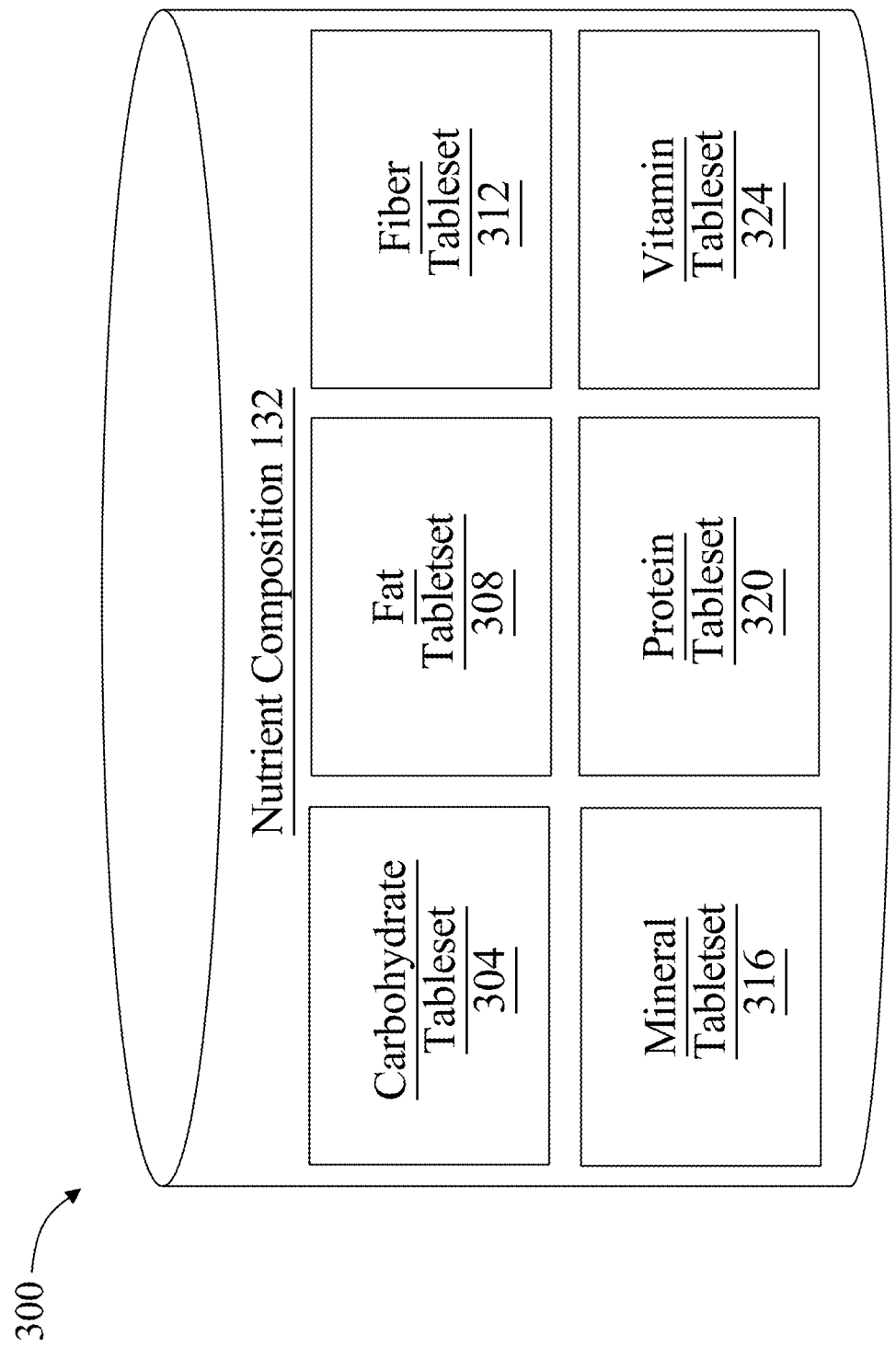
FIG. 3 is a representative diagram of an exemplary datastore of nutrient composition according to an embodiment of the invention.

Now referring to FIG. 3, an exemplary datastore 300 storing plurality of nutrient compositions 132 according to an embodiment of the invention is illustrated. Nutrient composition 132 may be implemented, without limitation, as a relational databank, a key-value retrieval databank such as a NOSQL databank, or any other format or structure for use as a databank that a person skilled in the art would recognize as suitable upon review of the entirety of this disclosure. Nutrient composition 132 may alternatively or additionally be implemented using a distributed data storage protocol and/or data structure, such as a distributed hash table or the like. Nutrient composition 132 may include a plurality of data entries and/or records as described above. Data entries in a databank may be flagged with or linked to one or more additional elements of information, which may be reflected in data entry cells and/or in linked tables such as tables related by one or more indices in a relational database. Persons skilled in the art, upon reviewing the entirety of this disclosure, will be aware of various ways in which data entries in a databank may store, retrieve, organize, and/or reflect data and/or records as used herein, as well as categories and/or populations of data consistently with this disclosure. Nutrient composition 132 may include a carbohydrate tableset 304. Carbohydrate tableset 304 may relate to a nourishment composition of an nutrition element with respect to the quantity and/or type of carbohydrates in the nutrition element. As a non-limiting example, carbohydrate tableset 304 may include monosaccharides, disaccharides, oligosaccharides, polysaccharides, and the like thereof. Nutrient composition 132 may include a fat tableset 308. Fat tableset 308 may relate to a nourishment composition of an nutrition element with respect to the quantity and/or type of esterified fatty acids in the nutrition element. Fat tableset 308 may include, without limitation, triglycerides, monoglycerides, diglycerides, phospholipids, sterols, waxes, and free fatty acids. Nutrient composition 132 may include a fiber tableset 312. Fiber tableset 312 may relate to a nourishment composition of a nutrition element with respect to the quantity and/or type of fiber in the nutrition element. As a non-limiting example, fiber tableset 312 may include soluble fiber, such as beta-glucans, raw guar gum, psyllium, inulin, and the like thereof as well as insoluble fiber, such as wheat bran, cellulose, lignin, and the like thereof. Nutrient composition 132 may include a mineral tableset 316. Mineral tableset 316 may relate to a nourishment composition of a nutrition element with respect to the quantity and/or type of minerals in the nutrition element. As a non-limiting example, mineral tableset 316 may include calcium, phosphorous, magnesium, sodium, potassium, chloride, sulfur, iron, manganese, copper, iodine, zing, cobalt, fluoride, selenium, and the like thereof. Nutrient composition 132 may include a protein tableset 320. Protein tableset 320 may relate to a nourishment composition of an nutrition element with respect to the quantity and/or type of proteins in the nutrition element. As a non-limiting example, protein tableset 320 may include amino acids combinations, wherein amino acids may include, without limitation, alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, valine, and the like thereof. Nutrient composition 132 may include a vitamin tableset 324. Vitamin tableset 324 may relate to a nourishment composition of a nutrition element with respect to the quantity and/or type of vitamins in the nutrition element. As a non-limiting example, vitamin tableset 324 may include vitamin A, vitamin $B_1$, vitamin $B_2$, vitamin $B_3$, vitamin $B_5$, vitamin $B_6$, vitamin $B_7$, vitamin $B_9$, vitamin $B_{12}$, vitamin C, vitamin D, vitamin E, vitamin K, and the like thereof.

Figure 4:
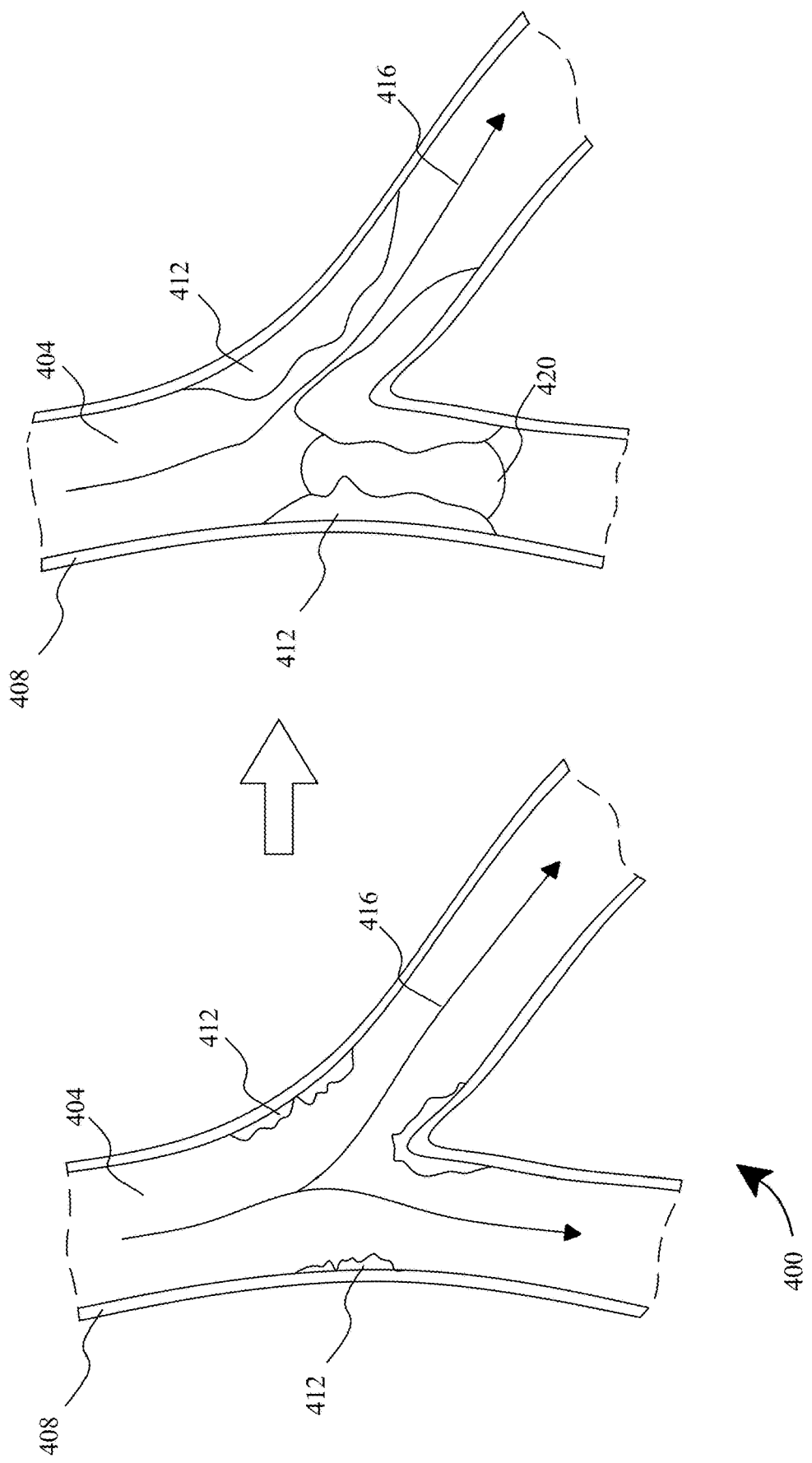
FIG. 4 is a representative diagram of an exemplary embodiment of biomarkers that can be received from a cardiovascular sample collection according to an embodiment of the invention.

Now referring to FIG. 4, an exemplary embodiment 400 of atherosclerosis biomarkers that may be received from cardiovascular sample 108 is illustrated in cross sectional view. One of ordinary skill in the art, after reviewing the entirety of this disclosure, would appreciate that this is only a non-limiting example of a biomarker that may be present in the herein disclosed system and method. Artery 404 is presented on the left with minimal atherosclerosis present, although it is there. Blood is present within artery that travels throughout the user's body with oxygenated blood to away from the heart to the body. Artery 404 is bounded radially by arterial wall 408. Fatty deposits 412 are presented in three places in both diagrams. In general, the build-up of fats, cholesterol, and other substances in and on the artery walls is referred to as atherosclerosis and causes a plurality of other health issues collectively referred to as cardiovascular disease. A buildup of cholesterol plaque in the arterial walls 408 which can cause obstruction of blood flow. Plaques may rupture causing acute occlusion of the artery by clot. "Acclusion", for the purposes of this disclosure, refers to the closure or obstruction of an artery or vein. Atherosclerosis often has no symptoms until a plaque ruptures or the buildup is severe enough to block blood flow. A healthy diet and exercise can help. Treatments include medications, procedures to open blocked arteries and surgery. An angioplasty, or a treatment for atherscloerosis in which a balloon and stent is used to restore blood flow to an artery 404 may be a biomarker consistent cardiovascular sample 108. Blood 416 may be collected as cardiovascular sample 108 as well for at least the reasons disclosed earlier in this paper, some of which, in a non-limiting example, may include blood tests, cholesterol level, blood pressure, chemical analysis, compound analysis, and the like. If atherosclerosis goes unchecked clot 120 may form, completely blocking blood flow leading to severe health problems like heart attack, stroke, damage to bodily systems, and even death. A biopsy of any of the artery's components, including blood 416 and clot 420 can be a biomarker consistent with the disclosure of cardiovascular sample 108.

Figure 5:
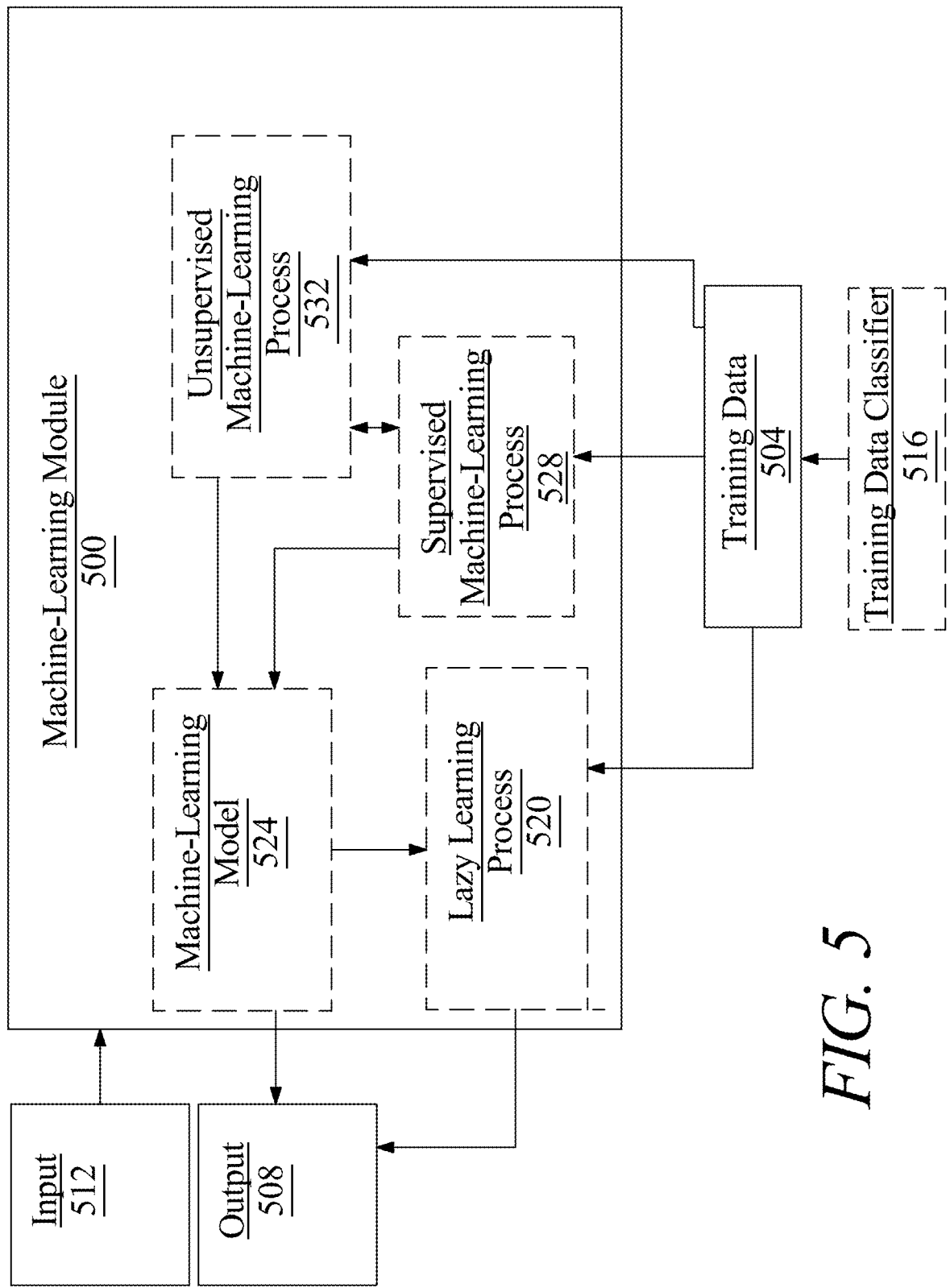
FIG. 5 is a block diagram of an exemplary embodiment of a machine-learning module.

Referring now to FIG. 5, an exemplary embodiment of a machine-learning module 500 that may perform one or more machine-learning processes as described in this disclosure is illustrated. Machine-learning module may perform determinations, classification, and/or analysis steps, methods, processes, or the like as described in this disclosure using machine learning processes. A "machine learning process," as used in this disclosure, is a process that automatedly uses training data 504 to generate an algorithm that will be performed by a computing device/module to produce outputs 508 given data provided as inputs 512; this is in contrast to a non-machine learning software program where the commands to be executed are determined in advance by a user and written in a programming language.

Still referring to FIG. 5, "training data," as used herein, is data containing correlations that a machine-learning process may use to model relationships between two or more categories of data elements. For instance, and without limitation, training data 504 may include a plurality of data entries, each entry representing a set of data elements that were recorded, received, and/or generated together; data elements may be correlated by shared existence in a given data entry, by proximity in a given data entry, or the like. Multiple data entries in training data 504 may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data 504 according to various correlations; correlations may indicate causative and/or predictive links between categories of data elements, which may be modeled as relationships such as mathematical relationships by machine-learning processes as described in further detail below. Training data 504 may be formatted and/or organized by categories of data elements, for instance by associating data elements with one or more descriptors corresponding to categories of data elements. As a non-limiting example, training data 504 may include data entered in standardized forms by persons or processes, such that entry of a given data element in a given field in a form may be mapped to one or more descriptors of categories. Elements in training data 504 may be linked to descriptors of categories by tags, tokens, or other data elements; for instance, and without limitation, training data 504 may be provided in fixed-length formats, formats linking positions of data to categories such as comma-separated value (CSV) formats and/or self-describing formats such as extensible markup language (XML), JavaScript Object Notation (JSON), or the like, enabling processes or devices to detect categories of data.

Alternatively or additionally, and continuing to refer to FIG. 5, training data 504 may include one or more elements that are not categorized; that is, training data 504 may not be formatted or contain descriptors for some elements of data. Machine-learning algorithms and/or other processes may sort training data 504 according to one or more categorizations using, for instance, natural language processing algorithms, tokenization, detection of correlated values in raw data and the like; categories may be generated using correlation and/or other processing algorithms. As a non-limiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name may be identified by reference to a list, dictionary, or other compendium of terms, permitting ad-hoc categorization by machine-learning algorithms, and/or automated association of data in the data entry with descriptors or into a given format. The ability to categorize data entries automatedly may enable the same training data 504 to be made applicable for two or more distinct machine-learning algorithms as described in further detail below. Training data 504 used by machine-learning module 500 may correlate any input data as described in this disclosure to any output data as described in this disclosure. As a non-limiting illustrative example nourishment scores and nutrient compositions may be inputs, wherein a nutrition element is outputted.

Further referring to FIG. 5, training data may be filtered, sorted, and/or selected using one or more supervised and/or unsupervised machine-learning processes and/or models as described in further detail below; such models may include without limitation a training data classifier 516. Training data classifier 516 may include a "classifier," which as used in this disclosure is a machine-learning model as defined below, such as a mathematical model, neural net, or program generated by a machine learning algorithm known as a "classification algorithm," as described in further detail below, that sorts inputs into categories or bins of data, outputting the categories or bins of data and/or labels associated therewith. A classifier may be configured to output at least a datum that labels or otherwise identifies a set of data that are clustered together, found to be close under a distance metric as described below, or the like. Machine-learning module 500 may generate a classifier using a classification algorithm, defined as a processes whereby a computing device and/or any module and/or component operating thereon derives a classifier from training data 504. Classification may be performed using, without limitation, linear classifiers such as without limitation logistic regression and/or naive Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers. As a non-limiting example, training data classifier 516 may classify elements of training data to classes of deficiencies, wherein a nourishment deficiency may be categorized to a large deficiency, a medium deficiency, and/or a small deficiency.

Still referring to FIG. 5, machine-learning module 500 may be configured to perform a lazy-learning process 520 and/or protocol, which may alternatively be referred to as a "lazy loading" or "call-when-needed" process and/or protocol, may be a process whereby machine learning is conducted upon receipt of an input to be converted to an output, by combining the input and training set to derive the algorithm to be used to produce the output on demand. For instance, an initial set of simulations may be performed to cover an initial heuristic and/or "first guess" at an output and/or relationship. As a non-limiting example, an initial heuristic may include a ranking of associations between inputs and elements of training data 504. Heuristic may include selecting some number of highest-ranking associations and/or training data 504 elements. Lazy learning may implement any suitable lazy learning algorithm, including without limitation a K-nearest neighbors algorithm, a lazy naïve Bayes algorithm, or the like; persons skilled in the art, upon reviewing the entirety of this disclosure, will be aware of various lazy-learning algorithms that may be applied to generate outputs as described in this disclosure, including without limitation lazy learning applications of machine-learning algorithms as described in further detail below.

Alternatively or additionally, and with continued reference to FIG. 5, machine-learning processes as described in this disclosure may be used to generate machine-learning models 524. A "machine-learning model," as used in this disclosure, is a mathematical and/or algorithmic representation of a relationship between inputs and outputs, as generated using any machine-learning process including without limitation any process as described above, and stored in memory; an input is submitted to a machine-learning model 524 once created, which generates an output based on the relationship that was derived. For instance, and without limitation, a linear regression model, generated using a linear regression algorithm, may compute a linear combination of input data using coefficients derived during machine-learning processes to calculate an output datum. As a further non-limiting example, a machine-learning model 524 may be generated by creating an artificial neural network, such as a convolutional neural network comprising an input layer of nodes, one or more intermediate layers, and an output layer of nodes. Connections between nodes may be created via the process of "training" the network, in which elements from a training data 504 set are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning.

Still referring to FIG. 5, machine-learning algorithms may include at least a supervised machine-learning process 528. At least a supervised machine-learning process 528, as defined herein, include algorithms that receive a training set relating a number of inputs to a number of outputs, and seek to find one or more mathematical relations relating inputs to outputs, where each of the one or more mathematical relations is optimal according to some criterion specified to the algorithm using some scoring function. For instance, a supervised learning algorithm may include nutrient compositions and/or nourishment scores as described above as inputs, nutrition elements as outputs, and a scoring function representing a desired form of relationship to be detected between inputs and outputs; scoring function may, for instance, seek to maximize the probability that a given input and/or combination of elements inputs is associated with a given output to minimize the probability that a given input is not associated with a given output. Scoring function may be expressed as a risk function representing an "expected loss" of an algorithm relating inputs to outputs, where loss is computed as an error function representing a degree to which a prediction generated by the relation is incorrect when compared to a given input-output pair provided in training data 504. Persons skilled in the art, upon reviewing the entirety of this disclosure, will be aware of various possible variations of at least a supervised machine-learning process 528 that may be used to determine relation between inputs and outputs. Supervised machine-learning processes may include classification algorithms as defined above.

Further referring to FIG. 5, machine learning processes may include at least an unsupervised machine-learning processes 532. An unsupervised machine-learning process, as used herein, is a process that derives inferences in datasets without regard to labels; as a result, an unsupervised machine-learning process may be free to discover any structure, relationship, and/or correlation provided in the data. Unsupervised processes may not require a response variable; unsupervised processes may be used to find interesting patterns and/or inferences between variables, to determine a degree of correlation between two or more variables, or the like.

Still referring to FIG. 5, machine-learning module 500 may be designed and configured to create a machine-learning model 524 using techniques for development of linear regression models. Linear regression models may include ordinary least squares regression, which aims to minimize the square of the difference between predicted outcomes and actual outcomes according to an appropriate norm for measuring such a difference (e.g. a vector-space distance norm); coefficients of the resulting linear equation may be modified to improve minimization. Linear regression models may include ridge regression methods, where the function to be minimized includes the least-squares function plus term multiplying the square of each coefficient by a scalar amount to penalize large coefficients. Linear regression models may include least absolute shrinkage and selection operator (LASSO) models, in which ridge regression is combined with multiplying the least-squares term by a factor of 1 divided by double the number of samples. Linear regression models may include a multi-task lasso model wherein the norm applied in the least-squares term of the lasso model is the Frobenius norm amounting to the square root of the sum of squares of all terms. Linear regression models may include the elastic net model, a multi-task elastic net model, a least angle regression model, a LARS lasso model, an orthogonal matching pursuit model, a Bayesian regression model, a logistic regression model, a stochastic gradient descent model, a perceptron model, a passive aggressive algorithm, a robustness regression model, a Huber regression model, or any other suitable model that may occur to persons skilled in the art upon reviewing the entirety of this disclosure. Linear regression models may be generalized in an embodiment to polynomial regression models, whereby a polynomial equation (e.g. a quadratic, cubic or higher-order equation) providing a best predicted output/actual output fit is sought; similar methods to those described above may be applied to minimize error functions, as will be apparent to persons skilled in the art upon reviewing the entirety of this disclosure.

Continuing to refer to FIG. 5, machine-learning algorithms may include, without limitation, linear discriminant analysis. Machine-learning algorithm may include quadratic discriminate analysis. Machine-learning algorithms may include kernel ridge regression. Machine-learning algorithms may include support vector machines, including without limitation support vector classification-based regression processes. Machine-learning algorithms may include stochastic gradient descent algorithms, including classification and regression algorithms based on stochastic gradient descent. Machine-learning algorithms may include nearest neighbors algorithms. Machine-learning algorithms may include Gaussian processes such as Gaussian Process Regression. Machine-learning algorithms may include cross-decomposition algorithms, including partial least squares and/or canonical correlation analysis. Machine-learning algorithms may include naïve Bayes methods. Machine-learning algorithms may include algorithms based on decision trees, such as decision tree classification or regression algorithms. Machine-learning algorithms may include ensemble methods such as bagging meta-estimator, forest of randomized tress, AdaBoost, gradient tree boosting, and/or voting classifier methods. Machine-learning algorithms may include neural net algorithms, including convolutional neural net processes.

Figure 6:
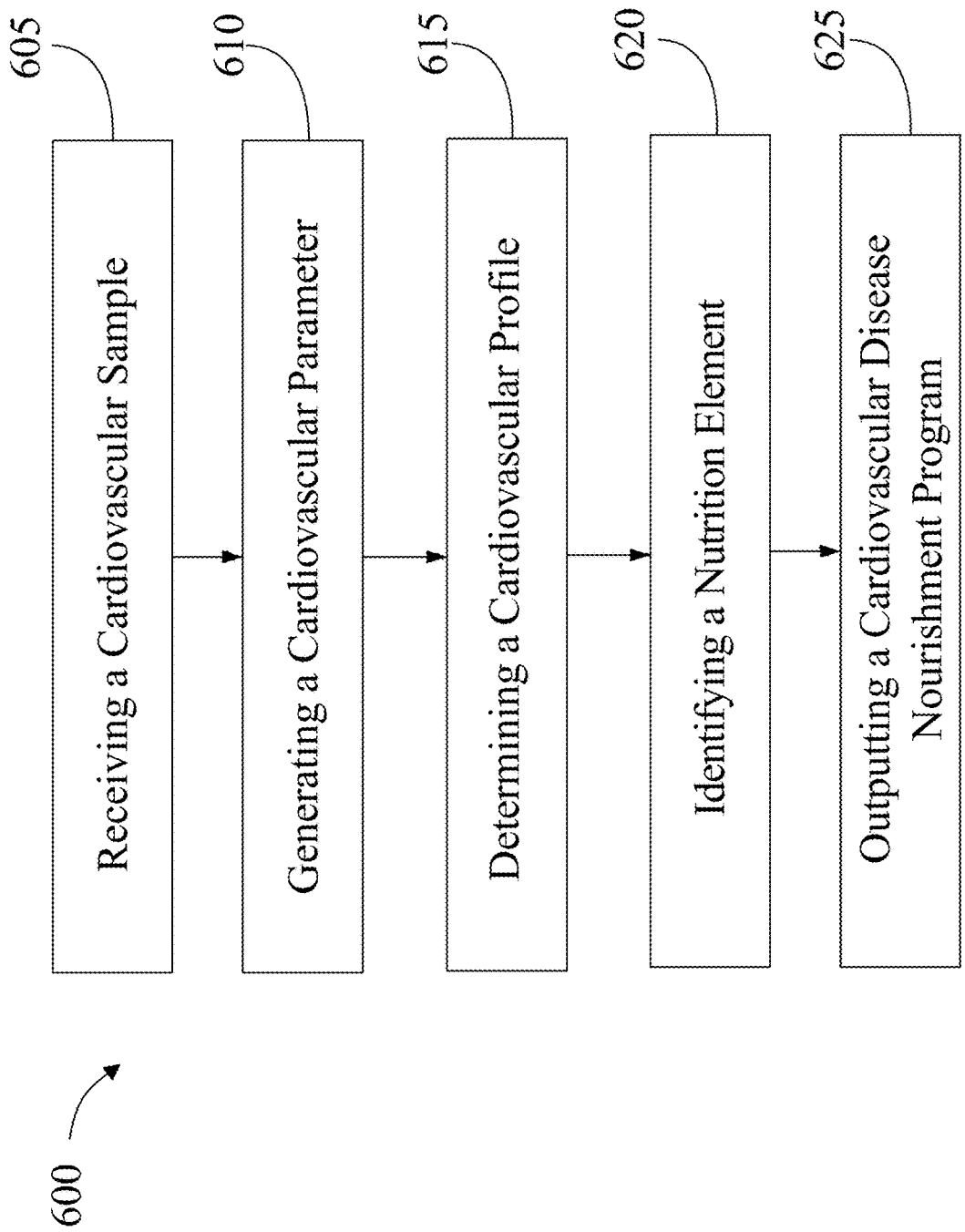
FIG. 6 is a process flow diagram illustrating an exemplary embodiment of a method of generating a cardiovascular disease nourishment program.

Referring now to FIG. 6, an exemplary method 600 for generating a cardiovascular disease nourishment program is presented. At step 605, a computing device 604 receives at least a cardiovascular sample 108 relating to a user. Computing device 104 includes any of the computing devices 104 as described herein. Cardiovascular sample 108 includes any of the cardiovascular samples 108 as described herein. For instance, and without limitation, cardiovascular sample 108 may include one or more blood samples, biopsies, prior diagnoses of cardiovascular disease, or tests results relating to a user.

Still referring to FIG. 6, at step 610, computing device 104 generates at least a cardiovascular parameter 112 of a plurality of cardiovascular parameters 112 as a function of the cardiovascular disease sample 108. Cardiovascular parameter 112 may be any cardiovascular parameter as described herein.

Still referring to FIG. 6, at step 615, computing device 104 determines a cardiovascular profile 116 as a function of the at least a cardiovascular parameter 112. The cardiovascular parameter 112 includes a numerical cardiovascular health score 120 correlated to at least a cardiovascular parameter 112. Cardiovascular profile 116 includes an atherosclerosis indicator 124 correlated to at least a cardiovascular parameter 112. Cardiovascular parameter 112 may be any cardiovascular parameter 112 as described herein. Cardiovascular health score 120 may be any cardiovascular health score 120 as described herein. Atherosclerosis indicator 124 may be any atherosclerosis indicator 124 as described herein.

Still referring to FIG. 6, at step 620, computing device 104 identifies at least a nutrition element 128 as a function of the cardiovascular profile 116. Nutrition element 128 may be any nutrition element 128 as described herein. Identifying at least a nutrition element 128 includes obtaining at least a nutrient composition 132 correlated to at least a nutrition element 128. Nutrient composition 132 may be any nutrient composition 132 as described herein. Identifying at least a nutrition element 128 includes determining a nourishment score 136 as a function of the effect of the nutrition element 128 on the cardiovascular profile 116. Nourishment score 136 may be any nourishment score 136 as described herein. Determining nourishment score 136 includes generating training data using the plurality of nutrition elements 128 identified according to the cardiovascular disease category. Training data may be any training data as described herein. Cardiovascular disease category may be any cardiovascular disease category as described herein. Training a nutrition element machine-learning model 140 according to the training data, wherein training data includes a plurality of data entries that correlates the nourishment score 136 for each cardiovascular disease category to nutrient composition 132. Computing device 104 determines nutrition score 136 as a function of the nutrition element machine-learning model 140 and cardiovascular profile 116. Computing device 104 includes identifying a nutrition element 128 as a function of the nutrient composition 132, nourishment score 136 and nutrition element machine-learning model 140. Identifying nutrition elements 128 may include classifying the cardiovascular profile 116 to a cardiovascular disease category and identifying the plurality of nutrition elements 128 according to the cardiovascular disease category. Identifying the plurality of nutrition elements 128 may include curating nutrition elements 128 intended to prevent cardiovascular disease according to the cardiovascular disease category.

Still referring to FIG. 6, at step 625, computing device 104 generates cardiovascular disease nourishment program 144 as a function of the cardiovascular profile 116, which includes cardiovascular health score 120 and atherosclerosis indicator 124. Generating the cardiovascular disease nourishment program 144 includes generating a nourishment program classifier using a classification machine-learning process to classify nutrient composition 132 to the plurality of nutrition elements 128. Generating nourishment program classifier may include compiling the plurality of nutrition elements to achieve the nourishment score 126. Generating the cardiovascular disease nourishment program 144 includes generating an adherence score. An "adherence score", for the purposes of this disclosure, is a quantitative value that reflects the level of user participation in the cardiovascular nourishment program 144. Adherence score may be any adherence score as described herein. Generating adherence score includes calculating a change in cardiovascular health score 120. Generating the cardiovascular disease nourishment program 144 may include receiving at least a user preference regarding the at least a nutrition element. The user preference may be any user preference as described herein. The user preference increases the adherence score. Generating adherence score may include modifying at least a nutrition element as a function of the at least a user preference. Modification may be any modification as described herein.

It is to be noted that any one or more of the aspects and embodiments described herein may be conveniently implemented using one or more machines (e.g., one or more computing devices that are utilized as a user computing device for an electronic document, one or more server devices, such as a document server, etc.) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

Figure 7:
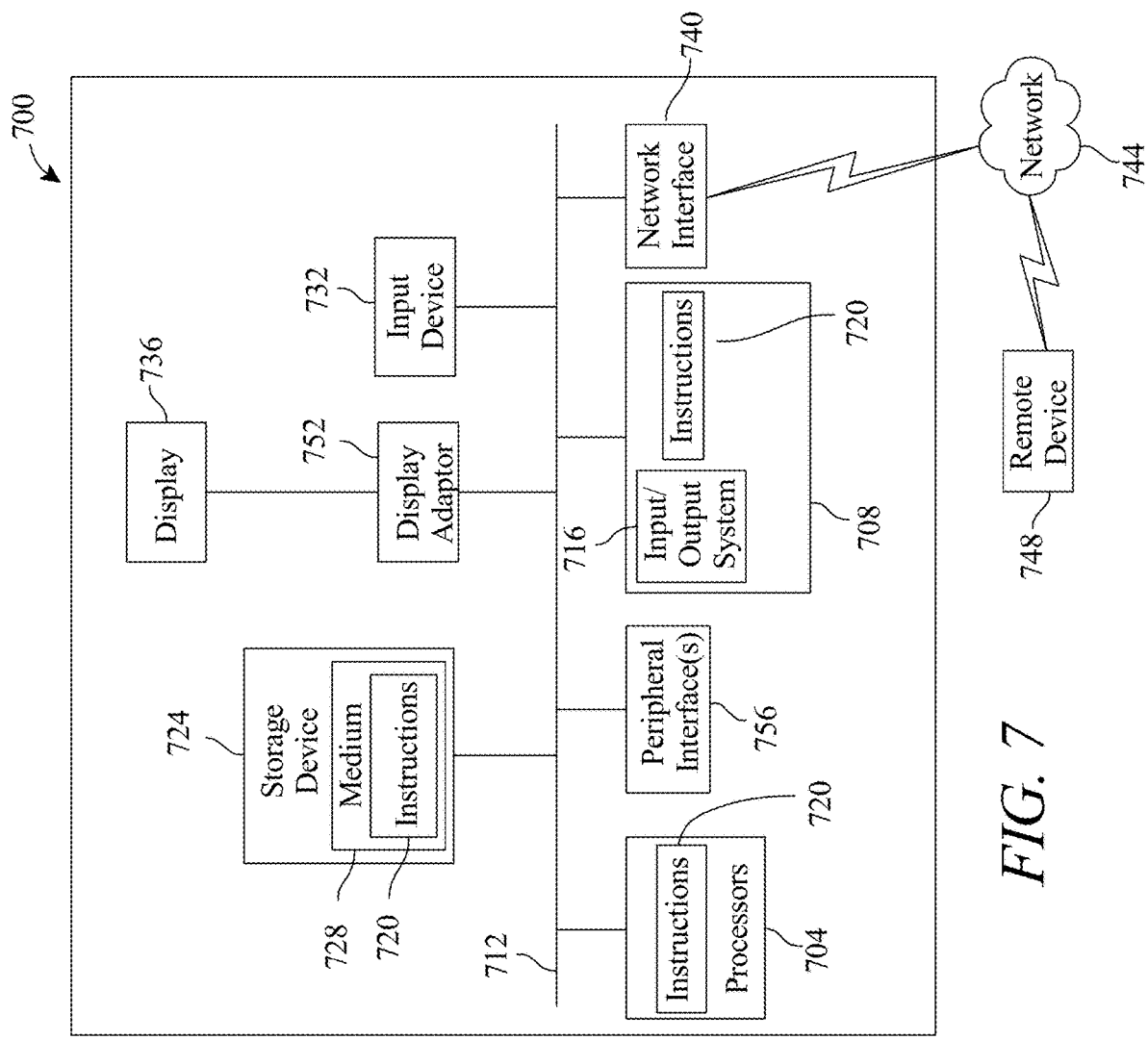
FIG. 7 is a block diagram of a computing system that can be used to implement any one or more of the methodologies disclosed herein and any one or more portions thereof.

FIG. 7 shows a diagrammatic representation of one embodiment of a computing device in the exemplary form of a computer system 700 within which a set of instructions for causing a control system to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 700 includes a processor 704 and a memory 708 that communicate with each other, and with other components, via a bus 712. Bus 712 may include any of several types of bus structures including, but not limited to, a memory bus, a memory controller, a peripheral bus, a local bus, and any combinations thereof, using any of a variety of bus architectures.

Processor 704 may include any suitable processor, such as without limitation a processor incorporating logical circuitry for performing arithmetic and logical operations, such as an arithmetic and logic unit (ALU), which may be regulated with a state machine and directed by operational inputs from memory and/or sensors; processor 704 may be organized according to Von Neumann and/or Harvard architecture as a non-limiting example. Processor 704 may include, incorporate, and/or be incorporated in, without limitation, a microcontroller, microprocessor, digital signal processor (DSP), Field Programmable Gate Array (FPGA), Complex Programmable Logic Device (CPLD), Graphical Processing Unit (GPU), general purpose GPU, Tensor Processing Unit (TPU), analog or mixed signal processor, Trusted Platform Module (TPM), a floating point unit (FPU), and/or system on a chip (SoC).

Memory 708 may include various components (e.g., machine-readable media) including, but not limited to, a random-access memory component, a read only component, and any combinations thereof. In one example, a basic input/output system 716 (BIOS), including basic routines that help to transfer information between elements within computer system 700, such as during start-up, may be stored in memory 708. Memory 708 may also include (e.g., stored on one or more machine-readable media) instructions (e.g., software) 720 embodying any one or more of the aspects and/or methodologies of the present disclosure. In another example, memory 708 may further include any number of program modules including, but not limited to, an operating system, one or more application programs, other program modules, program data, and any combinations thereof.

Computer system 700 may also include a storage device 724. Examples of a storage device (e.g., storage device 724) include, but are not limited to, a hard disk drive, a magnetic disk drive, an optical disc drive in combination with an optical medium, a solid-state memory device, and any combinations thereof. Storage device 724 may be connected to bus 712 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 724 (or one or more components thereof) may be removably interfaced with computer system 700 (e.g., via an external port connector (not shown)). Particularly, storage device 724 and an associated machine-readable medium 728 may provide nonvolatile and/or volatile storage of machine-readable instructions, data structures, program modules, and/or other data for computer system 700. In one example, software 720 may reside, completely or partially, within machine-readable medium 728. In another example, software 720 may reside, completely or partially, within processor 704.

Computer system 700 may also include an input device 732. In one example, a user of computer system 700 may enter commands and/or other information into computer system 700 via input device 732. Examples of an input device 732 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 732 may be interfaced to bus 712 via any of a variety of interfaces (not shown) including, but not limited to, a serial interface, a parallel interface, a game port, a USB interface, a FIREWIRE interface, a direct interface to bus 712, and any combinations thereof. Input device 732 may include a touch screen interface that may be a part of or separate from display 736, discussed further below. Input device 732 may be utilized as a user selection device for selecting one or more graphical representations in a graphical interface as described above.

A user may also input commands and/or other information to computer system 700 via storage device 724 (e.g., a removable disk drive, a flash drive, etc.) and/or network interface device 740. A network interface device, such as network interface device 740, may be utilized for connecting computer system 700 to one or more of a variety of networks, such as network 744, and one or more remote devices 748 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 744, may employ a wired and/or a wireless mode of communication. In general, any network topology may be used. Information (e.g., data, software 720, etc.) may be communicated to and/or from computer system 700 via network interface device 740.

Computer system 700 may further include a video display adapter 752 for communicating a displayable image to a display device, such as display device 736. Examples of a display device include, but are not limited to, a liquid crystal display (LCD), a cathode ray tube (CRT), a plasma display, a light emitting diode (LED) display, and any combinations thereof. Display adapter 752 and display device 736 may be utilized in combination with processor 704 to provide graphical representations of aspects of the present disclosure. In addition to a display device, computer system 700 may include one or more other peripheral output devices including, but not limited to, an audio speaker, a printer, and any combinations thereof. Such peripheral output devices may be connected to bus 712 via a peripheral interface 756. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve methods, systems, and software according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions and additions may be made to that which is specifically disclosed herein without departing from the spirit and scope of the present invention

What is claimed is:

1. A system for generating a cardiovascular disease nourishment program, the system comprising:
   a computing device, the computing device configured to:
   receive at least a cardiovascular sample relating to a user;
   generate at least a cardiovascular parameter as a function of the at least a cardiovascular sample;
   determine a cardiovascular profile as a function of the at least a cardiovascular parameter and at least a cardiovascular deficiency, wherein:
      the at least a cardiovascular deficiency is compared to a cardiovascular threshold;
      the cardiovascular profile comprises a numerical cardiovascular health score correlated to the at least a cardiovascular parameter; and
      the cardiovascular profile comprises an atherosclerosis indicator correlated to the at least a cardiovascular parameter, wherein the atherosclerosis indicator includes a location in a user's body wherein a vein or artery is accumulating plaque buildup;
   identify at least a nutrition element as a function of the cardiovascular profile, wherein identifying comprises:
      obtaining at least a nutrient composition correlated to at least a nutrition element;
      determining a nourishment score as a function of the effect of the nutrition element on the cardiovascular profile; and
      identifying the at least a nutrition element as a function of the nourishment score and a nutrition element machine-learning model, wherein identifying the at least a nutrition element further comprises:
         training the nutrition element machine-learning model using a nutrition element training set, received as a function of user entered valuations of nourishment compositions, nourishment deficiencies, and nutrition elements and previously determined correlations of nourishment compositions and nourishment deficiencies, correlating the at least a nourishment composition and nourishment deficiency to a nutrition element, and wherein the nutrition element machine-learning model inputs nourishment compositions and nourishment deficiencies and outputs a nutrition element; and
   generate a cardiovascular disease nourishment program as a function of the nourishment score, at least a classification machine-learning process, and the cardiovascular profile, wherein generating the cardiovascular disease nourishment program further comprises:
      training the at least a classification machine-learning process as a function of a nourishment training set and wherein the cardiovascular disease nourishment program includes the cardiovascular health score and the atherosclerosis indicator.

2. The system of claim 1, wherein receiving at least the cardiovascular sample comprises receiving a result of one or more tests relating the user.

3. The system of claim 1, wherein receiving at least the cardiovascular sample comprises receiving a prior diagnosis of a cardiovascular disease relating to the user.

4. The system of claim 1, wherein identifying the plurality of nutrition elements comprises:
   classifying the cardiovascular profile to a cardiovascular disease category; and
   identifying the plurality of nutrition elements according to the cardiovascular disease category.

5. The system of claim 4, wherein identifying the plurality of nutrition elements comprises curating nutrition elements intended to prevent cardiovascular disease according to the cardiovascular disease category.

6. The system of claim 5, wherein determining nourishment scores comprises:
   generating training data using the nutrient elements identified according to the cardiovascular disease category;
   training a nutrition element machine-learning model according to the training data, wherein training data includes a plurality of data entries that correlates the at least a nutrient composition for each cardiovascular disease category to nourishment score; and
   determining nourishment scores as a function of the nutrition element machine-learning model and the cardiovascular profile.

7. The system of claim 1, wherein generating the cardiovascular disease nourishment program comprises:
   training a nourishment classifier as a function of a classification machine-learning process and a training set relating the at least a nutrient composition and nourishment score to nutrition elements; and
   outputting the nourishment program classifier as a function of the nutrition elements, the at least a nutrient composition, and nourishment score.

8. The system of claim 1, wherein the computing device is further configured to generate an adherence score, wherein the adherence score reflects the level of user participation in the cardiovascular nourishment program.

9. The system of claim 8, wherein generating the adherence score comprises calculating a change in the numerical cardiovascular health score.

10. The system of claim 1, wherein generating the cardiovascular disease nourishment program comprises:
    receiving at least a user preference regarding the at least a nutrition element;
    wherein the at least a user preference increases the adherence score; and
    modifying the at least a nutrition element as a function of the at least a user preference.

11. A method for generating a cardiovascular disease nourishment program, the method comprising:
    receiving, by a computing device at least a cardiovascular disease sample relating to a user;
    generating, by the computing device, at least a cardiovascular parameter as a function of the cardiovascular sample;

determining, by the computing device, a cardiovascular profile as a function of the at least a cardiovascular parameter and at least a cardiovascular deficiency;
  wherein the at least a cardiovascular deficiency is compared to a cardiovascular threshold;
  wherein the cardiovascular profile comprises a numerical cardiovascular health score correlated to the at least a cardiovascular parameter;
  wherein the cardiovascular profile comprises an atherosclerosis indicator correlated to the at least a cardiovascular parameter, wherein the atherosclerosis indicator includes a location in a user's body wherein a vein or artery is accumulating plaque buildup;
identifying, by the computing device, at least a nutrition element as a function of the cardiovascular profile, wherein identifying comprises:
  obtaining at least a nutrient composition correlated to at least a nutrition element;
  determining a nourishment score as a function of the effect of the nutrition element on the cardiovascular profile; and
  identifying the at least a nutrition element as a function of the nourishment score, and nutrition element machine-learning model, wherein identifying the at least a nutrition element further comprises:
    training the nutrition element machine-learning model using a nutrition element training set, received as a function of user entered valuations of nourishment compositions, nourishment deficiencies, and nutrition elements and previously determined correlations of nourishment compositions and nourishment deficiencies, correlating the at least a nourishment composition and nourishment deficiency to a nutrition element, and wherein the nutrition element machine-learning model inputs nourishment compositions and nourishment deficiencies and outputs a nutrition element; and
  generating, by the computing device, a cardiovascular disease nourishment program as a function of the nourishment score, at least a classification machine-learning process, and the cardiovascular profile, wherein generating the cardiovascular disease nourishment program:
    training the at least a classification machine-learning process as a function of a nourishment training set and wherein the cardiovascular disease nourishment program includes the cardiovascular health score and the atherosclerosis indicator.

12. The method of claim 11, wherein receiving at least the cardiovascular sample comprises receiving a result of one or more tests relating the user.

13. The method of claim 11, wherein receiving at least the cardiovascular sample comprises receiving a prior diagnosis of a cardiovascular disease relating to the user.

14. The method of claim 11, wherein identifying the plurality of nutrition elements comprises:
  classifying the cardiovascular profile to a cardiovascular disease category; and
  identifying the plurality of nutrition elements according to the cardiovascular disease category.

15. The method of claim 14, wherein identifying the plurality of nutrition elements comprises curating nutrition elements intended to prevent cardiovascular disease according to the cardiovascular disease category.

16. The method of claim 15, wherein determining nourishment scores comprises:
  generating training data using the nutrient elements identified according to the cardiovascular disease category;
  training a nutrition element machine-learning model according to the training data, wherein training data includes a plurality of data entries that correlates the at least a nutrient composition for each cardiovascular disease category to nourishment score; and
  determining nourishment scores as a function of the nutrition element machine-learning model and the cardiovascular profile.

17. The method of claim 11, wherein generating the cardiovascular disease nourishment program comprises:
  training a nourishment classifier as a function of a classification machine-learning process and a training set relating the at least a nutrient composition and nourishment score to nutrition elements; and
  outputting the nourishment program classifier as a function of nutrition elements, the at least a nutrient composition, and nourishment score.

18. The method of claim 11, wherein the computing device is further configured to generate the adherence score, wherein the adherence score reflects the level of user participation in the cardiovascular nourishment program.

19. The method of claim 18, wherein generating the adherence score comprises calculating a change in the numerical cardiovascular health score.

20. The method of claim 11, wherein generating the cardiovascular disease nourishment program comprises:
  receiving at least a user preference regarding the at least a nutrition element;
  wherein the at least a user preference increases the adherence score; and
  modifying the at least a nutrition element as a function of the at least a user preference.

* * * * *